United States Patent [19]

Smith

[11] Patent Number: 4,829,980
[45] Date of Patent: May 16, 1989

[54] TRIGGER DEVICE FOR HEAT PACK

[76] Inventor: Martin L. Smith, 4 Gunner La., Rubery, Birmingham, United Kingdom

[21] Appl. No.: 52,737
[22] PCT Filed: Aug. 26, 1986
[86] PCT No.: PCT/GB86/00506
§ 371 Date: Apr. 21, 1987
§ 102(e) Date: Apr. 21, 1987
[87] PCT Pub. No.: WO87/01275
PCT Pub. Date: Mar. 12, 1987

[30] Foreign Application Priority Data

Aug. 28, 1985 [GB] United Kingdom ............... 8521349

[51] Int. Cl.⁴ .............................................. F24J 1/00
[52] U.S. Cl. .................................................. 126/263
[58] Field of Search ............... 126/263, 204, 400, 206; 422/245; 44/3.1; 128/399-403

[56] References Cited

U.S. PATENT DOCUMENTS

| | | | |
|---|---|---|---|
| 1,915,523 | 6/1933 | Ferguson | 126/263 |
| 2,220,777 | 11/1940 | Othmer | 126/204 |
| 4,077,390 | 3/1978 | Stanley et al. | 126/263 |
| 4,379,448 | 4/1983 | Kapralis et al. | 126/263 |
| 4,460,546 | 7/1984 | Kapralis et al. | 126/263 |
| 4,580,547 | 4/1986 | Kapralis et al. | 126/263 |
| 4,587,950 | 5/1986 | Mack et al. | 126/263 |

FOREIGN PATENT DOCUMENTS 599756 11/1931 Fed. Rep. of Germany ...... 126/263

Primary Examiner—James C. Yeung
Attorney, Agent, or Firm—Berman, Aisenberg & Platt

[57] ABSTRACT

A trigger device for a heat pack comprises three helically-coiled, resilient metallic filaments (1,2,3) nested one within the other and of inwardly decreasing diameter, the filament (2) being wound in a sense opposite to that of filaments (1) and (3). Flexing the assembly of nested helices about its longitudinal axes produces a rubbing action action between adjacent turns thereof which initiates crystallization. Other devices comprises two nested helices wound in the same sense; a single helix having a pressure plate at one end and an external or internal cap at the other; and a body of randomly convoluted or woven metallic filament.

14 Claims, 4 Drawing Sheets

TRIGGER DEVICE FOR HEAT PACK

This invention concerns improvements in and relating to trigger or activator devices for so-called 'heat packs'.

In the so-called 'heat packs' latent heat of crystallisation is stored in a supercooled solution of a crystalline material. It is known that such packs can be stored in a stable condition and used as a heat source as and when required, by triggering or initiating crystallisation of the supercooled solution whereby the latent heat of crystallisation is given up in the resulting exothermic reaction. British Patent Specification No. 1585808, for example, describes a self-contained heat pack comprising a flexible container incorporating the appropriate supercooled solution, together with an activator device in the form of a fissured activator strip capable of being flexed to initiate crystallization of the solution.

U.S. Pat. No. 2,220,777 describes a heat pack comprising a container, which may have rigid or flexible walls, for the supercooled solution and an activator device which may take the form of a rod having one end which is attached to a flexible wall portion and is manipulable to cause the other end to scrape the inside of the container wall; in another embodiment opposed wall portions of a flexible container are provided with metal inserts which may be manipulated so that their internal surfaces come come into scraping contact. In yet another, rather conjectural, embodiment 'various pieces of metal' may be placed within the container and crystallisation initiated merely by shaking the container.

Although various activator devices for initiating such crystallisation have hitherto been proposed, the mechanism whereby crystallisation is initiated is not fully understood.

It is an object of the present invention to provide a reliable activator device for initiating crystallisation of a supercooled solution, for example in a so-called 'heat pack'.

An activator device in accordance with the invention is characterised in that it comprises one or more convoluted metallic filaments to disposed that flexing of the filamentary metallic material, and consequent rubbing contact of contacting metallic surfaces, is effective to initiate crystallisation of a supercooled solution within which the activator device may be immersed.

According to a first preferred form of the invention the activator device comprises two or more resilient helical filaments nested one within the other, optionally with a flexible core. Each helix may be wound in a sense the same as or opposed to that of its immediate neighbours; moreover the diameter of the filaments may decrease in a radially inward direction. According to a second preferred form of the invention the device comprises a helical spring fitted with a cap or terminal insert, the surface of which is brought into rubbing contact with that of the spring on compression, extension or flexing thereof. In a third preferred form the device comprises a body of flexible convoluted filament which may be random or woven.

In each form of the invention flexing of the convoluted flexible metallic filaments, for example the one or more springs, causes the rubbing contact which triggers crystallisation. In the case of the first and third forms of the invention the contact is between surfaces of convoluted flexible filament and in the second form between the surface of the convoluted flexible filament (the spring) and the insert or cap.

An activator device in accordance with the invention may take a variety of forms, some specific examples of the invention being illustrated in the accompanying drawings, in which FIG. 1 is a side elevation of one embodiment of device according to the invention;

Figure 1:
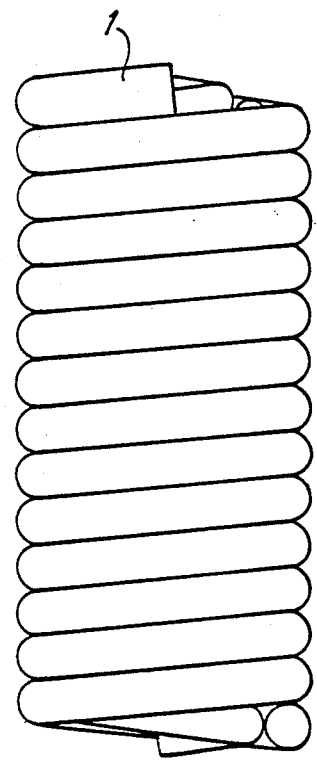
Figure 2:
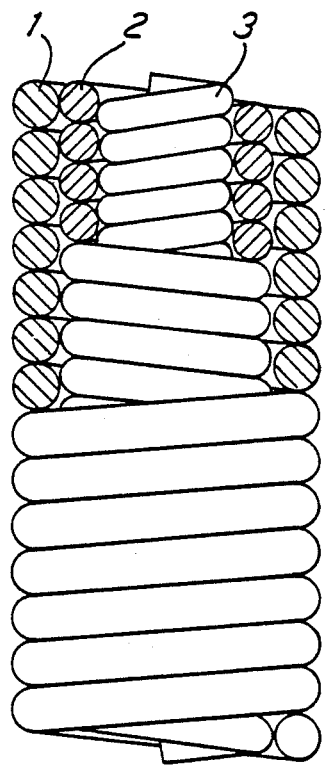
FIG. 2 is a part sectional elevation corresponding to FIG. 1.
Figure 3:
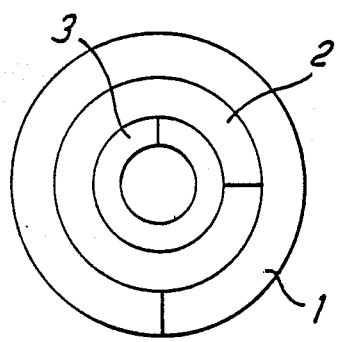
FIG. 3 is a plan view corresponding to FIG. 1.

Referring to FIGS. 1 to 3, there is shown a device intended for immersion within the supercooled solution retained within the outer envelope of a heat pack, the heat pack, apart from the presence of the activator of FIGS. 1 to 3, being of known construction and therefore not illustrated. The activator device comprises three helically coiled metallic filaments 1,2,3, nested one within the other. The helical filaments possess an inherent spring characteristic tending to retain the helices of the nested filaments symmetrical about a rectilinear longitudinal axis, whilst permitting bending of the assembly of the nested filaments against this restoring force. As in the case of known arrangments, the flexible wall of the outer envelope of the heat pack (not shown) is such as to enable manipulation of the activator device. It will be appreciated that the action of flexing the assembly of nested helices is such as to produce a rubbing action between the adjacent turns thereof, this being sufficient to initiate crystallisation of the surrounding supercooled solution. It will be noted that the configuration of the nested helices is such that each helix is wound in a sense that is in opposition to that of the adjacent inner and/or outer helix. It will be further noted that the respective diameters of the filaments forming the helices are different from one another, being reduced in a direction towards the central longitudinal axis of the assembly, such that whereas each helix is of approximately the same axial length, each helix has a smaller pitch and thus a correspondingly greater number of turns than the neighbouring outer helix.

Figure 4:
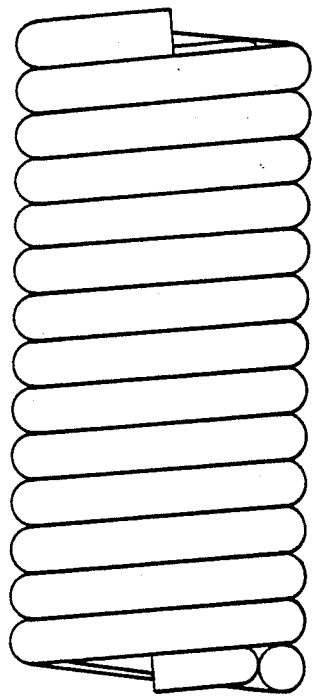
FIGS. 4, 5 and 6 are views corresponding to FIGS. 1 to 3 respectively and illustrating another embodiment of the invention.
Figure 5:
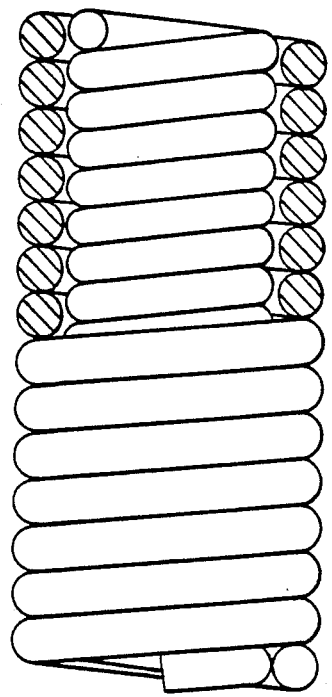
Figure 6:
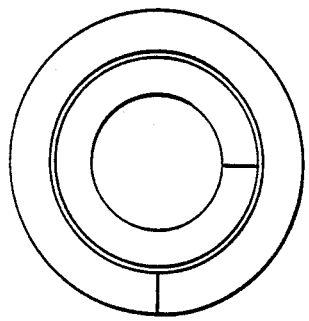

It will be seen that the arrangement of FIGS. 4 to 6 is essentially similar to that of FIGS. 1 to 3, with the exception that only two helical metallic filaments are provided, both being wound in the same sense. The method of operation of the device is otherwise similar to that of FIGS. 1 to 3.

Figure 7:
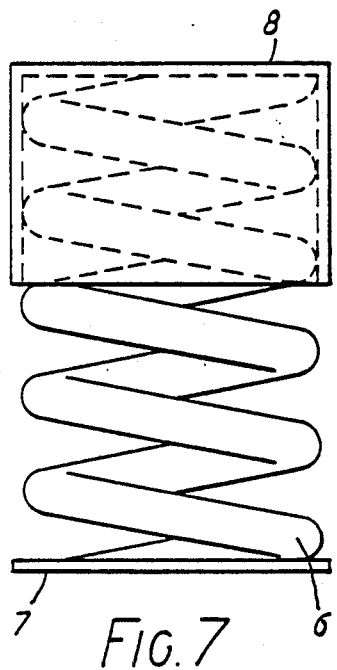
FIGS. 7, 8 and 9 are corresponding views of a yet further embodiment of the invention.
Figure 8:
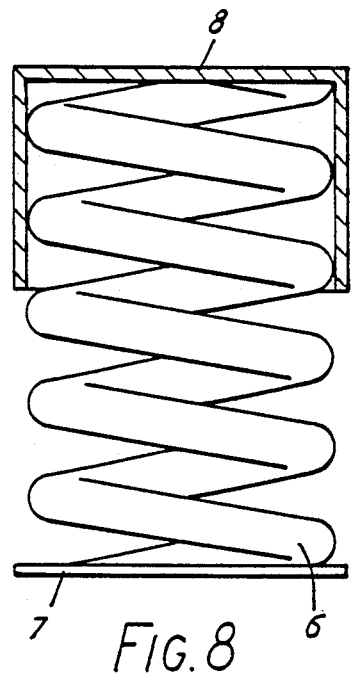
Figure 9:
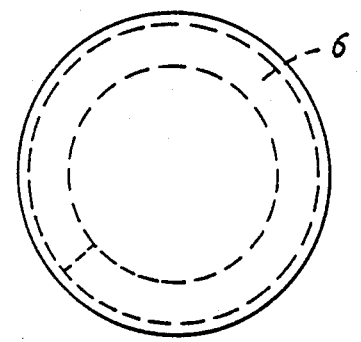

The device of FIGS. 7 to 9 comprises a single helical metallic compression spring 6, at one end of which is located a circular pressure plate 7. The other end of the spring is enclosed within a generally cylindrical end cap 8 the internal surface of which is in rubbing contact with the outer periphery of the adjacent helices of the spring. In operation of the device, compression of the end cap towards the pressure plate 7 and/or relative angular movement of the pressure plate 7 and end cap 8 is effective to cause friction between the contacting metallic surfaces, in order to activate crystallisation of the surrounding super-cooled liquid.

Figure 10:
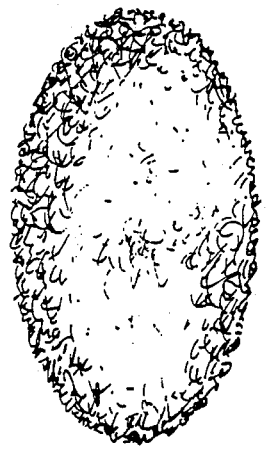
FIGS. 10, 11 and 12 are each an elevation of a yet further embodiment of device in accordance with the invention.
Figure 11:
Figure 12:

FIGS. 10 to 12 show activators comprising randomly convoluted metallic filament, such as wire wool, forming a body of material the compression and/or flexing of which is sufficient to effect crystallisation of the surrounding liquid. In each case the body of material forms a coherent structure having the shape illustrated, the structure being disposed within larger outer envelope of the heat pack itself.

In any of the above described embodiments, the filamentary material may be confined within a sleeve or apertured envelope of resilient rubber or like material in order to cover any sharp edges of the filamentary material and thus prevent puncture of the outer envelope of the heat pack, whilst allowing the required flexing of the activator assembly.

The various embodiments of activator described above provide varying degrees of sensitivity of actuation. That is to say the degree of flexing of the actuator required to trigger crystallisation of a given solution will be less as the sensitivity is increased. In general the sensitivity of the activator device is increased by increasing the overall area of contact between metallic surfaces, reducing the localised areas of contact and/or increasing the local contact pressure. Thus factors tending to increase sensitivity of the activator include: increased number of nested helices (FIGS. 1 to 6); nested helices of opposite pitch (FIGS. 1 to 3); reduced diameter of metal filament; tighter interengagement of windings of nested helices; smaller pitch of wound helix.

It will be appreciated from the above disclosure that the invention accordingly provides a reliable and versatile activator arrangement having a response capable of being tailored to suit the requirements of a given design of heat pack. Moreover, the activator device according to the invention lends itself to being housed in a small compartment separate from, but in fluid communication with, the main compartment of a flexible walled container containing the working solution.

Various modification and alterations may be made to the illustrated embodiments of the invention without departing from the underlying inventive concept. Thus, for example, in the arrangement of FIGS. 7 to 9 the end cap 8 may be replaced by a metallic body located within the spring 6. In the arrangements of FIGS. 10 to 12, the randomly convoluted filament may be woven in a regular manner.

I claim:

1. A heat pack comprising a container having a flexible wall, a supercooled solution in said container, and a self-contained flexible metal activator immersed in said supercooled solution, a first surface portion on a convoluted filament of said flexible metal activator being in contact with a second surface portion of said flexible metal activator and wherein flexing said flexible metal activator causes said first surface portion to rub against said second surface portion and initiate crystallization of said solution.

2. A heat pack according to claim 1 wherein said flexible metal activator comprises a plurality of nested helical elements.

3. A heat pack according to claim 2 wherein a first of said nested helical elements is wound in a direction opposite to that of a second of said nested helical elements.

4. A heat pack according to claim 3 wherein said nested helical elements are wound in the same directions.

5. A heat pack according to claim 2, 3, or 4 wherein the diameter of said helical elements decreases along a longitudinal axis.

6. A heat pack according to claim 1 wherein said flexible metal activator comprises a compression spring and a cap or insert having a surface portion in contact with a surface portion of said spring.

7. A heat pack according to claim 1 wherein said flexible metal activator comprises a multiplicity of metal fibers.

8. An activator for initiating crystallization of a supercooled solution comprising a first convoluted metal filament having a first surface portion and a second convoluted metal filament having a second surface portion in contact with said first surface portion and wherein flexing said filament causes said first and second surface portions to rub together and initiate crystallization.

9. A device as claimed in claim 8 wherein said metal filament comprises a multiplicity of fibres in woven form.

10. A device as claimed in claim 8 wherein said metal filament comprises an assembly of two or more helical elements nestled one within the other.

11. A device as claimed in claim 10, wherein each helical element is wound in a sense that is opposed to that of each adjacent helical element.

12. A device as claimed in claim 10, wherein each helical element is wound in a sense that is the same as that of each adjacent helical element.

13. A device as claimed in claim 10, 11 or 12, wherein the diameter of each helical element decreases in a direction along the longitudinal axis of the assembly.

14. A device as claimed in claim 8 wherein said metal filament comprises a multiplicity of fibres in random convoluted form.

* * * * *